US008666758B2

(12) United States Patent (10) Patent No.: US 8,666,758 B2
DiMaggio et al. (45) Date of Patent: Mar. 4, 2014

(54) METHOD OF DISPENSING PHARMACEUTICALS

(75) Inventors: John P. DiMaggio, Powell, OH (US); Mary Edith Potts-Hozlock, Glenside, PA (US); Thomas Joseph Weiss, Cherry Hill, NJ (US)

(73) Assignee: Omnicare, Inc., Covington, KY (US)

( * ) Notice: Subject to any disclaimer, the term of this patent is extended or adjusted under 35 U.S.C. 154(b) by 2460 days.

(21) Appl. No.: 10/949,070

(22) Filed: Sep. 24, 2004

(65) Prior Publication Data

US 2005/0187791 A1 Aug. 25, 2005

Related U.S. Application Data

(63) Continuation-in-part of application No. 10/610,681, filed on Jul. 2, 2003.

(51) Int. Cl.
*G06Q 10/00* (2012.01)
(52) U.S. Cl.
USPC .................................................. 705/2; 705/3
(58) Field of Classification Search
USPC ........................................................ 705/2, 3
See application file for complete search history.

(56) References Cited

U.S. PATENT DOCUMENTS

| | | | | |
|---|---|---|---|---|
| 4,476,381 A * | 10/1984 | Rubin | ............................ | 235/375 |
| 4,478,658 A | 10/1984 | Wittwer | | |
| 4,548,825 A | 10/1985 | Voss et al. | | |
| 4,587,407 A | 5/1986 | Ahmed et al. | | |
| 4,835,372 A * | 5/1989 | Gombrich et al. | ............ | 235/375 |
| 4,918,604 A * | 4/1990 | Baum | ............................... | 221/5 |
| 5,401,059 A | 3/1995 | Ferrario | | |
| 5,597,995 A * | 1/1997 | Williams et al. | ............... | 235/375 |
| 5,666,492 A * | 9/1997 | Rhodes et al. | ..................... | 705/3 |
| 5,700,998 A | 12/1997 | Palti | | |
| 5,758,095 A | 5/1998 | Albaum et al. | | |
| 5,857,713 A | 1/1999 | Horimoto | | |
| 5,963,453 A * | 10/1999 | East | ............................... | 700/244 |
| 6,112,182 A | 8/2000 | Akers et al. | | |
| 6,529,801 B1 * | 3/2003 | Rosenblum | .................... | 700/237 |
| 6,769,228 B1 * | 8/2004 | Mahar | ............................ | 53/411 |
| 6,976,628 B2 * | 12/2005 | Krupa | ....................... | 235/462.08 |
| 7,124,031 B1 * | 10/2006 | Hoffman et al. | ................. | 702/19 |
| 2001/0001144 A1 | 5/2001 | Kapp | | |
| 2002/0010595 A1 * | 1/2002 | Kapp | ............................... | 705/2 |
| 2002/0029223 A1 * | 3/2002 | Rice et al. | ................... | 707/104.1 |
| 2002/0069088 A1 | 6/2002 | Berg | | |
| 2002/0077865 A1 * | 6/2002 | Sullivan | ............................ | 705/3 |
| 2002/0143582 A1 * | 10/2002 | Neuman et al. | .................... | 705/3 |
| 2003/0050802 A1 | 3/2003 | Jay et al. | | |
| 2003/0144883 A1 | 7/2003 | Fagerholm et al. | | |

(Continued)

OTHER PUBLICATIONS

Informational literature entitled "Workflow QS1"; by J.M. Smith Corporation, 1 page (2002).

*Primary Examiner* — Lena Najarian
(74) *Attorney, Agent, or Firm* — Ostrolenk Faber LLP

(57) ABSTRACT

A method for electronically assisting in dispensing pharmaceuticals to long-term patient care facilities is provided. The method includes entering data associated with a prescription order into a system including an intervention database. Based on features of the order, an intervention from the intervention database is associated with the order, the intervention being associated with a route through the system. Data associated with the prescription order is routed along the route associated with the intervention.

16 Claims, 10 Drawing Sheets

(56) References Cited

U.S. PATENT DOCUMENTS

| | | |
|---|---|---|
| 2004/0006490 A1 | 1/2004 | Gingrich et al. |
| 2004/0006491 A1 | 1/2004 | Brown et al. |
| 2004/0019502 A1 | 1/2004 | Leaman et al. |
| 2004/0069849 A1* | 4/2004 | Stevens et al. ............... 235/385 |
| 2004/0138921 A1* | 7/2004 | Broussard et al. ............... 705/2 |

* cited by examiner

GENERIC SEQUENCE CODE LIST

| DESCRIPTION | GENERIC. SEQUENCE | LABEL WARNING CODE | OVERRIDE LABEL WARNING CODE |
|---|---|---|---|
| ALCOHOL-PROPYLENE GLYCOL TOP LOTN | 007085 | 0020 | |
| BENZOCAINE-CHLOROXYLENOL 5%-0.1% TOP OINT | 016644 | 0020 | |
| BENZOCAINE-CHLOROXYLENOL TOP AERO | 007463 | 0020 | |
| BENZOCAINE-CHLOROXYLENOL TOP AERO | 007463 | 0020 | |
| BENZOCAINE-CHLOROXYLENOL-HC 14 mg-1 mg-10 mg/mL OTIC DROP | 048610 | 0028 | |
| BORIC ACID-PROPYLENE GLYCOL TOP LIQD | 007101 | 0020 | |
| CHILDREN'S TYLENOL 160 mg/5 mL ORAL SUSP | 016947 | 0008 0092 0066 0070 | |

PRESS ANY KEY TO CONTINUE ......

FIG. 5

LABEL WARNING CODES LIST

| ID | FDS | OVERRIDE |
|---|---|---|
| | DESCRIPTION | DESCRIPTION |

0001 MAY CAUSE DROWSINESS. ALCOHOL MAY INTENSIFY THIS EFFECT. USE CARE WHEN OPERATING A CAR OR DANGEROUS MACHINES.

0002 IMPORTANT: FINISH ALL THIS MEDICATION UNLESS OTHERWISE DIRECTED BY PRESCRIBER.

0003 TAKE MEDICATION ON AN EMPTY STOMACH ONE HOUR BEFORE OR TWO TO THREE HOURS AFTER A MEAL UNLESS OTHERWISE DIRECTED BY YOUR DOCTOR.

0004 DO NOT TAKE DAIRY PRODUCTS, ANTACIDS, OR IRON PREPARATIONS WITHIN ONE HOUR OF THIS MEDICATION.

0005 MEDICATION SHOULD BE TAKEN WITH PLENTY OF WATER.

0006 MAY CAUSE DISCOLORATION OF THE URINE OR FECES.

0008 DO NOT DRINK ALCOHOLIC BEVEREGES WHEN TAKING THIS MEDICATION.

0009 SOME NON-PRESCRIPTION DRUGS MAY AGGRAVATE YOUR CONDITION. READ ALL LABELS CAREFULLY. IF A WARNING

PRESS ANY KEY TO CONTINUE....

FIG. 6

| DWF0027 | ORDER STATUS DISPLAY | 10/31 |
|---|---|---|
| | COMPANY : 2 VALLEYBROOK PHARMACY | |

| Rx NUMBER | : R37981 | FILL DATE | : 10/31/2003 | CURRENT STATUS | : MANIFEST |
|---|---|---|---|---|---|
| DELIVERY CODE | : AFTERNOON | | | DELIVERY TOTE | : 123 |
| FACILITY #/NAME | : 57 FACILITY FOR COMPANY 4 | | | STATION | : TESTWING// |
| PATIENT #/NAME | : 6 CLARK, BILL | | | TRANS. TYPE | : NEW |
| ITEM DESCRIPTION | : VANCOMYCIN 125 Mg CAPSULE | | | SHIPPED QTY | : 30 |
| SIG DIRECTIONS | : 1 CAP PO QD | | | | |

| ORDER ENTERED | : MBRAUN | AT | 11:49am | ON | 10/30/2003 | | |
|---|---|---|---|---|---|---|---|
| PV1 BATCH | : ENTERED BY RPh MJB | | | | | | |
| PV1 HELD | : | | | | | | |
| PV1 VERIFIED | : TWEISS | AT | 11:57am | ON | 10/30/2003 | | |
| LABELED | : KLYALL | AT | 11:59am | ON | 10/30/2003, | BATCH #2567, | 1 LABEL |
| LAST PV2 SCAN | : JACCHION | AT | 1:22pm | ON | 10/30/2003, | 1 of 1 SCAN | |
| LAST TOTE SCAN | : MBRAUN | AT | 02:36pm | ON | 10/30/2003, | 1 of 1 SCAN | |
| MANIFESTED | : MBRAUN | AT | 02:36pm | ON | 10/30/2003, | BATCH # 1473 | |

ENTER (F)INISHED WHEN DONE VIEWING ORDER

FIG. 10

DWF0013     ORDER STATUS DISPLAY     10/31
COMPANY 1 RESCOT LTC PHARMACY

| DELIVERY CODE | 1 ENTERED QOR/LTCP | 2 PV1 READY | 3 HELD | 4 BILL PEND | 5 REJECT | 6 LABEL ALLOWED | 7 LABELED | 8 PV2 | 9 TOTE SCAN | 10 MANIFEST |
|---|---|---|---|---|---|---|---|---|---|---|
| 1. CYCLE | 0/ 0 | 0 | 0 | 0 | 0 | 0 | 0 | 0 | 0 | 0 |
| 2. MSO | 0/ 0 | 0 | 0 | 0 | 0 | 0 | 0 | 1 | 0 | 0 |
| 3. PM | 0/ 0 | 0 | 0 | 0 | 0 | 1 | 0 | 0 | 0 | 0 |
| 4. SEVEN77 | 0/ 0 | 0 | 0 | 0 | 0 | 0 | 0 | 0 | 0 | 0 |
| 5. RED | 0/ 0 | 6 | 3 | 0 | 0 | 34 | 0 | 0 | 0 | 0 |
| 6. WHITE | 0/ 0 | 0 | 0 | 3 | 0 | 11 | 0 | 0 | 0 | 0 |
| 7. DEFAULT | 0/ 0 | 0 | 0 | 6 | 7 | 99 | 0 | 0 | 0 | 0 |
| 8. BLACK | 0/ 0 | 0 | 0 | 1 | 0 | 1 | 0 | 0 | 0 | 0 |
| 9. 9PM | 0/ 0 | 0 | 0 | 0 | 0 | 0 | 0 | 0 | 0 | 0 |
| TOTAL | 0/ 0 | 6 | 3 | 10 | 7 | 146 | 0 | 1 | 0 | 0 |

ENTER A COLUMN NUMBER TO DETAIL A STATUS, (R)EFRESH SCREEN, (PL)PRINT LABELS, (PM)PRINT MANIFESTS, <ENTER> TO SEE MORE DELIVERY CODES, OR '/' TO EXIT

FIG. 11

METHOD OF DISPENSING PHARMACEUTICALS

CROSS REFERENCE TO RELATED APPLICATIONS

This application is a continuation-in-part of application Ser. No. 10/610,681 filed Jul. 2, 2003.

TECHNICAL FIELD

The present application relates to methods and systems for electronic assistance in the dispensing of pharmaceuticals.

BACKGROUND

Long-term care pharmacies service long-term patient care facilities, such as skilled nursing, assisted living, subacute care, hospice, mental health, adult day care, correctional, home health, and board and care facilities. These long-term care pharmacies employ a variety of processes and systems filling a relatively high volume of incoming prescription orders. The processes and systems help to reduce errors not only by the pharmacies, but also by the prescribers. For example, systems have been proposed that have drug interaction and patient information stored in a database. A prescription order can be entered into the system and a computer can determine whether the currently prescribed medication may have an adverse interaction with any of the patient's previously prescribed medication.

SUMMARY

In an aspect, a method for electronically assisting in dispensing pharmaceuticals to long-term patient care facilities is provided. The method includes entering data associated with a prescription order into a system including an intervention database. Based on features of the order, an intervention from the intervention database is associated with the order, the intervention being associated with a route through the system. Data associated with the prescription order is routed along the route associated with the intervention.

In some embodiments, the intervention includes an identifier that identifies a route through the system. The identifier can be in the form of a numeric, alphabetic or alphanumeric code.

In certain embodiments, the system includes at least two networked computers. The step of routing data associated with the prescription order can include routing data associated with the prescription order from a first computer to a second computer. In some embodiments, the data associated with the prescription order is entered into the system using a computer.

In some cases, the method includes verifying that the data entered is consistent with the associated prescription order. An electronic edit list can be generated for use in the step of verifying. In some embodiments, the method includes tracking the order using barcode technology.

In some embodiments, the method can include, based on the data, detecting discontinuation of medication to a patient and associating an intervention with the order if discontinuation of medication is detected.

In another aspect, a computer implemented process for dispensing pharmaceuticals to long-term patient care facilities is provided. The process includes entering data relating to a batch of new prescription orders into fields of a computer system. The fields receive data relating to a pre-selected set of features of respective new prescription orders. The new prescription orders of the batch are classified into a first class of new prescription orders and a second class of new prescription orders based on the data entered. Data associated with the first class of new prescription orders is routed along a first route through the computer system and data associated with the second class of new prescription orders is routed along a second route through the computer system, the second route being different than the first route.

In some embodiments, the step of entering data is performed by a pharmacist. In some cases, the method includes determining whether to associate with respective new prescription orders one or more interventions based on the data. The first class of new prescription orders can consist of new prescription orders having an associated clinical intervention. The second class of new prescription orders can comprise new prescription orders having an associated non-clinical intervention.

In some embodiments, the method further includes detecting discontinuation of medication to a patient. In some cases, at least one of the first and second classes of new prescription orders consists of new prescription orders having no associated intervention.

In certain embodiments, the step of entering data includes entering a note into the computer system, the note being associated with a respective new prescription order. The step of routing data associated with the first class of new prescription orders can include routing the note associated with the respective new prescription order.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 5 is an embodiment of a generic sequence code list for use in the process of FIG. 1;

FIG. 6 is an embodiment of a partial label warning codes list for use in the process of FIG. 1;

FIG. 10 illustrates an embodiment of an order status screen for use in the process of FIG. 1; and FIG. 11 illustrates another embodiment of an order status screen for use in the process of FIG. 1.

DETAILED DESCRIPTION

Figure 1:
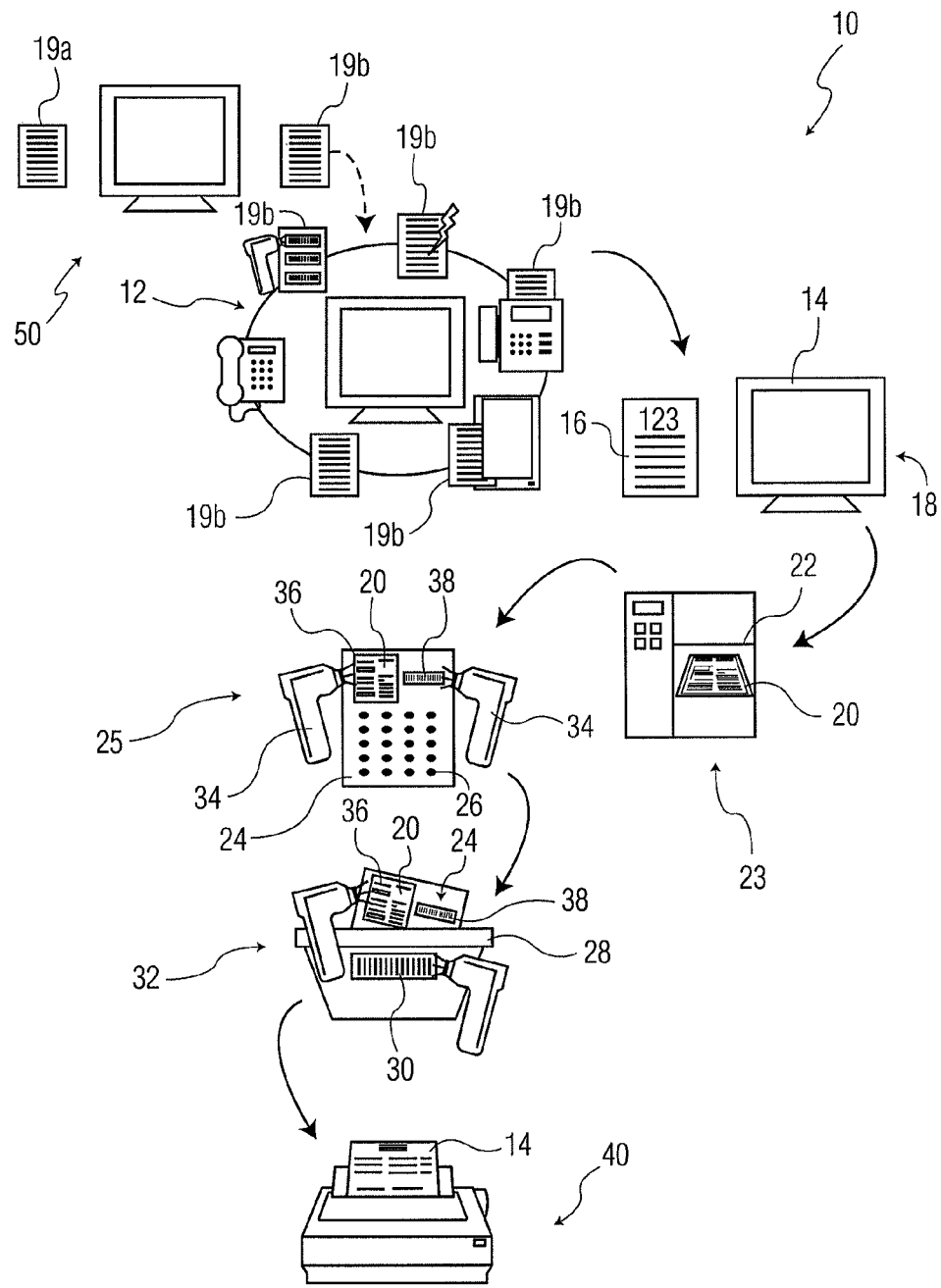
FIG. 1 is a flowchart illustrating an embodiment of a process for dispensing pharmaceuticals.

Referring to FIG. 1, a process 10 utilizes a system for assistance in dispensing pharmaceuticals to long-term patient care facilities. As used herein, a "system" may include any combination of components, such as hardware, software and/or firmware, used to perform or to assist in the performance of specified functions and the components may be physically located at differing locations or at the same location and some or all of the components may be connected through a wired or wireless network or the Internet.

Process Overview from Order Entry

The process 10 includes order entry 12 where a prescription order 19 is entered into the system (e.g., via facsimile image, barcode hardcopy, e-refill list, barcoded refill list, document imaging, telephone order). Typically, order entry staff having a non-clinical background performs order entry, however, other configurations are possible, such as, in some embodiments, order entry by a technician, a pharmacist or a pharmaceutical intern. As will be described in greater detail below, data associated with the prescription order and entered into the system can be appropriately routed through the system to efficiently complete the order by minimizing the amount of non-clinical tasks performed by the pharmacists.

After the prescription order (or, in some cases, a batch of prescription orders) has been entered into the system (e.g., at a computer workstation, for example, using a personal computer, laptop or hand-held device having fields for data entry), the order entry technician sends a command to a printer (not shown) to print an edit list 16 that contains information useable by downstream users, such as data from order entry, interventions identified based on features of the order and other important information. In an alternative embodiment, the edit list is in digital form and is relayed and displayed on a display device such as a monitor 14 of a computer. In some cases, orders may be routed through the system in a batch. As used herein a "batch" refers to a set of orders grouped together, e.g., by destination, for group delivery.

Figure 4:
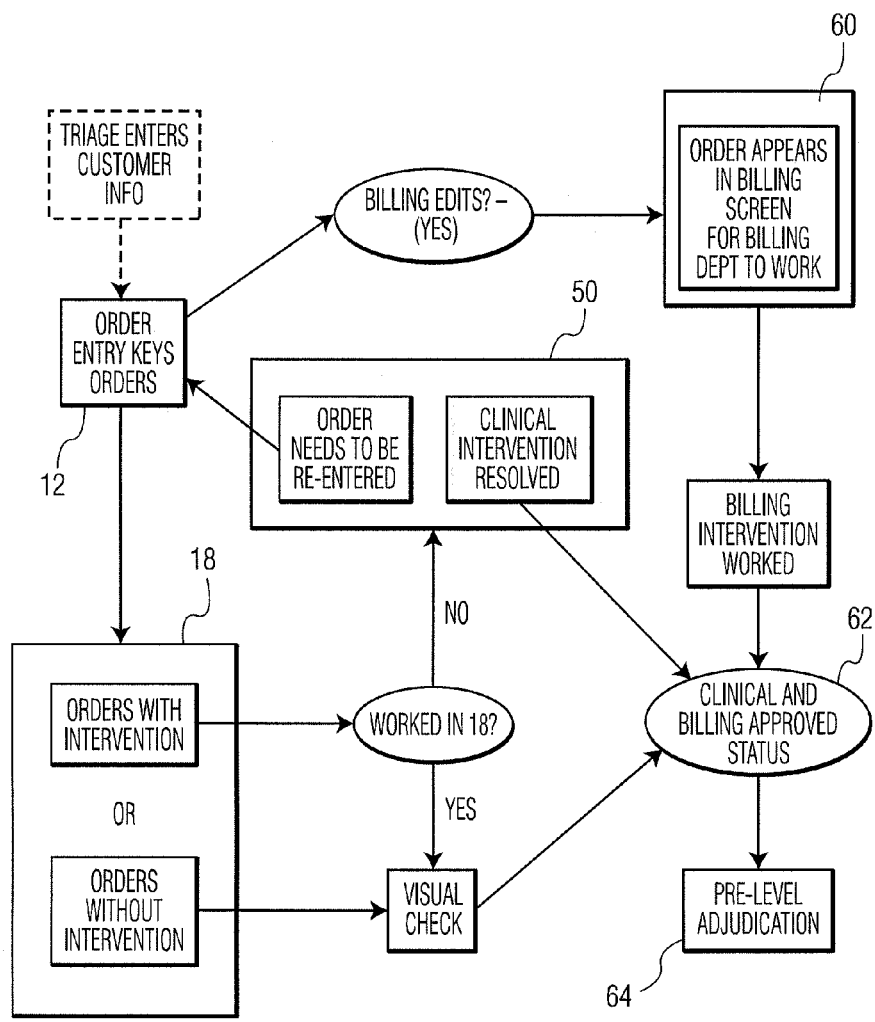
FIG. 4 is an embodiment of a workflow for use in the process of FIG. 1.

The edit list 16 and the original order 19 are compared by an order verifying pharmacist (e.g., by visual check and/or barcode scan) at an order verification step 18. In cases where the edit list 16 is in digital form, the order verification may be done completely on screen. In cases where the original order is in paper form, a digital copy of the original order 19 can be made, for example using a document imaging system connected to the system and the digital copy can be made available to the verifying pharmacist on screen for order verification 18. In other cases, the paper original order 19 may be made available to the verifying pharmacist to verify the edit list 16. If an intervention is associated with the order, the order verifying pharmacist may work (i.e., respond to) the intervention. When applicable, an intervention may be displayed on screen along with other data associated with an order (FIG. 4, for example). An "intervention", as used herein, refers to information such as a warning or other statement associated with an order that calls for an action that may be performed by a user. Interventions are generated based on an analysis (e.g., by a computer processor and/or by a user) of features of the order. As will be described in greater detail below, interventions may call for either a clinical action or a non-clinical action. By "clinical action", we mean an action that should be performed by a user having a requisite degree of pharmaceutical training or, in some cases, a user being supervised by a supervisor having a requisite degree of pharmaceutical training. A "non-clinical action" refers to any other action not requiring pharmaceutical training. During the order verification step 18, the pharmacist may, for example, verify, make changes, delete, re-route or put an order on hold by, e.g., entering such a command into the system.

In some embodiments, referring still to FIG. 1, if the verifying pharmacist verifies an order at order verification step 18 and the order is properly adjudicated (i.e., a believable payor has been identified), the order is routed to a label allowed queue and a prescription label 20 is permitted to be printed. A technician (or other user) can send a command to a label printer 22 and a prescription label 20 can be printed with an affixed barcode corresponding to the prescription order at a product picking step 23. The printed label 20 can then be affixed to a product package 24 containing a quantity of product 26 corresponding to the prescription order. The prescription label 20 includes a barcode and identifies the medication, the patient and the patient care facility.

To verify that the type of product and quantity of product matches the type and quantity of product identified by the prescription order, a product verification pharmacist, at a product verification step 25, reviews the product 26 and the label 20 and a comparison is made with data associated with the order and entered into the system at order entry 12. As shown, this is accomplished by use of a barcode scanner 34 capable of scanning barcodes 36, 38 associated with the prescription label and the product package, respectively. The barcode scanner is connected to the system and the information scanned is compared to the information entered into the system and verified at the order verification step 18.

Delivery totes 28 (or other suitable containers such as bags) can be used in transporting filled orders. The totes 28 are typically housed on a rack (not shown) and each includes information corresponding to a delivery destination. In this case, each tote 28 includes a barcode 30 located on the delivery tote. At a tote verification step 32, a user (e.g., a technician or pharmacist) takes a prescription package 24 including the prescription label 20 and performs a scan of the barcode 36 of the prescription label 20, of the barcode 38 of the package 24 and of the barcode 30 located on the delivery tote 28 using a barcode scanner 34 to verify that the correct order is associated with the correct tote 28. In some embodiments, an indicator (not shown), such as sound, display screen, etc., may be placed near or connected directly to the respective tote and activated by the system to indicate the appropriate delivery tote 28 for that successfully scanned product. If there are scan errors (e.g., wrong drug, wrong tote), the prescription may be set aside for a pharmacist review. The scan of the barcode 30 coupled with scans of the barcodes 36 and 38 aid in the placement of the correct order into the correct tote for delivery to the correct location. Upon completion of the verification step 32, packing list 40 is generated by delivery tote for all orders successfully scanned into the associated delivery tote. In some embodiments, the packing list 40 includes a barcode to be scanned along with the respective tote 28.

As an alternative to separate steps each performed by different users, the verification steps 25 and 32 can be performed as a single step (not shown) by, e.g., by a single pharmacist or technician with ad hoc review by a pharmacist. This can eliminate the need for a separate tote verification step by a technician.

Figure 2:
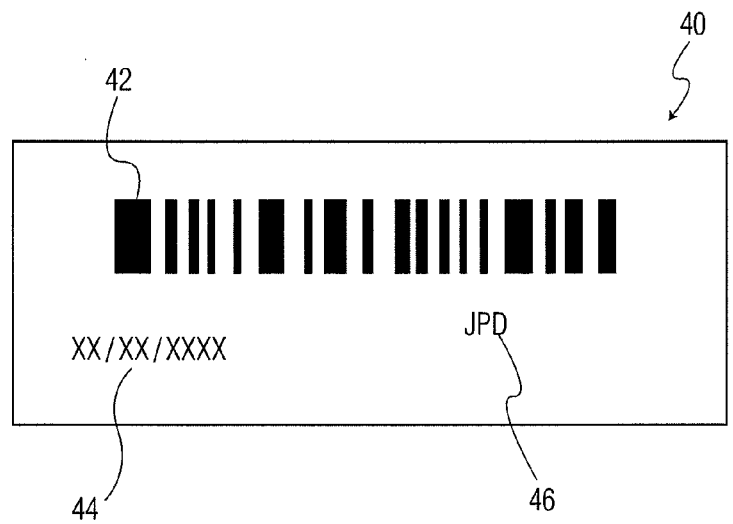
FIG. 2 is an embodiment of a barcode for use in the process of FIG. 1.

In some cases, a product package 24 may not have an associated barcode. In these cases, a portable programmable barcode generator (not shown) may be used by a pharmacist to place a barcode on the package once the pharmacist has verified that the product packaged and the quantity of product is correct. The item can then be placed along with the generated barcode with other items to be scanned and placed into a tote 28 for delivery. In certain embodiments, when a technician scans an order having a barcode generated by a pharmacist in the manner described above, the system can recognize the difference between a generated barcode and a package barcode 38. The system may display information indicating that a pharmacist performed a visual check of the product on the prescription label. Referring to FIG. 2, a pharmacist-generated label 40 includes a unique barcode 42 that includes a pharmacist ID number and a unique sequence number, a date 44 in human readable form and a pharmacist's initials 46 in human readable form. The system can be configured to allow the prescription label to be scanned only once and only on the day the label is printed.

In some embodiments, the label may be printed only after successful product identification, such as an electronic scan of the barcode printed on the product package. After the product identification procedure is completed, the system can allow for printing of a label directed to only that product identified by the product identification procedure. This can be useful in embodiments where a user picks products from a pick list of products generated based on the products ordered and can improve labeling reliability by requiring a product identification procedure prior to printing the label.

Pre-Order Entry Review

Referring back to FIG. 1, in some embodiments, prior to order entry 12, a triage pharmacist performs a pre-order entry review 50 of an incoming prescription order to classify orders, e.g., based on the presence or absence of clinical and/or non-clinical interventions or other issues (see elements 19a and 19b). This can allow identification of orders 19a that need clarification prior to order entry, e.g., to provide an opportunity to clarify those orders before proceeding to order entry, and can also allow orders 19b that can be processed immediately to proceed immediately to order entry. Pre-order entry review 50 by the triage pharmacist can increase the efficiency of the dispensing process, e.g., by allowing staff users at order entry 12 to strictly process orders and allowing pharmacist review by a pharmacist at the order verification step 18 to be primarily an accuracy review.

To assist in classifying orders, the triage pharmacist can enter into the system (e.g., at a computer workstation, for example, using a personal computer, laptop or hand-held device) selected data corresponding to a prescription order into the system. The amount of data entered by the triage pharmacist can, in some embodiments, be only that data necessary to conduct preliminary clinical and non-clinical reviews of the order, such as identifying drug-drug interactions, drug-allergy interactions and therapeutic interchange opportunities based on a pre-selected formulary. The remaining data for completing the order can be entered downstream at order entry 12, e.g., by order entry staff, for example, once it is determined that the order can proceed to order entry. The system analyzes the selected data to identify if the order is new, a refill or refill with changes, for clinical and financial warnings, etc. Based on this analysis, the order is classified and based on the classification the order may or may not proceed to order entry.

In addition to classifying an order, the triage pharmacist may also enter electronic notes associated with the order into the system, such as comments regarding analysis of the data, contact information and steps taken to satisfy an intervention, as examples. The notes can be routed along with the order through the system, e.g., to be accessed by a downstream user such as the verifying pharmacist and saved along with other prescription order information.

Figure 3:
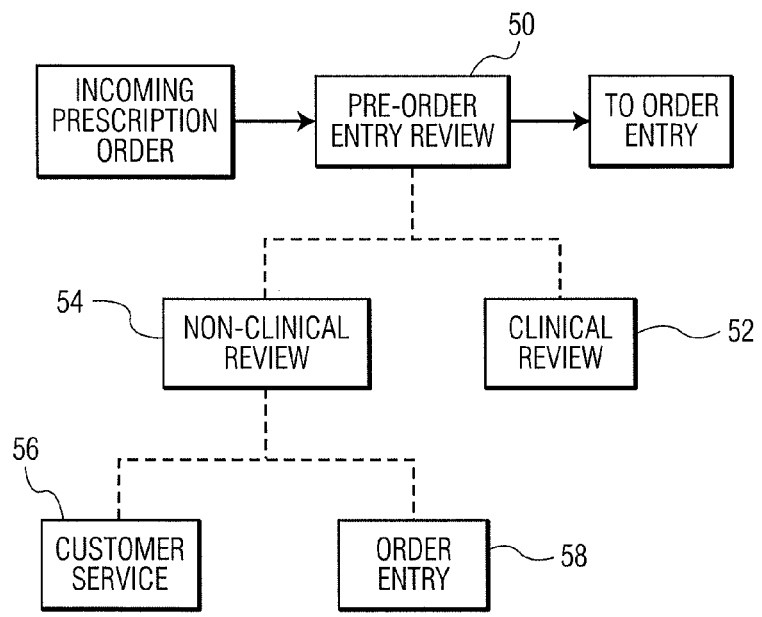
FIG. 3 is a diagram of a pre-order entry embodiment for use in the process of FIG. 1.

Referring to FIG. 3, to classify, route and/or work orders prior order entry, the triage pharmacist may perform both clinical 52 and non-clinical 54 tasks. The non-clinical tasks 54 may be divided into customer service tasks 56 and order entry tasks 58. Examples of clinical tasks include, for example, communicating with facilities (e.g., nursing homes, hospitals) regarding, for example, clinical medication issues (e.g., drugs, dosages, interactions, etc.), undertaking care planning, prioritizing activities to optimize workflow, reviewing orders of new facilities and interacting with order entry staff and verifying pharmacists. Examples of customer service tasks include, for example, prioritization of customer service requests (e.g., by department, urgency and action required to respond), researching questions, issues and incidents, preparing incident reports and overseeing quality control. Examples of order entry tasks include, for example, collection of facsimiles, prioritizing and sorting new and refill orders, reviewing orders for completeness, interacting with billing, initiating clinical services, researching questions for clinical pharmacist, reviewing orders of new facilities and providing filing/clerical support. In some embodiments, a technician performs some or all of the non-clinical review 54 while a pharmacist performs all of the clinical and, in some cases, some of the non-clinical tasks.

System Workflow Routing

For use in routing data through the system to an appropriate user, interventions associated with an order may have one or more identifiers, such as a numeric, alphabetic, or alphanumeric identifying code. The code can be used by the system to identify the appropriate route through the system (e.g., by comparing the code to a table including associated routes). For example, referring to FIG. 4, if at order entry 12 the system identifies a billing warning and, as a result, associates an appropriate, non-clinical intervention with the order, the code assigned to the intervention can indicate that the intervention along with associated data is to be routed to billing so that a user can satisfy the intervention. Similarly, if at order entry 12 the system identifies a clinical warning and, as a result, associates an appropriate clinical intervention with the order, the code assigned to the intervention can indicate that the intervention along with associated data is to be routed to the verifying pharmacist at verification 18. As noted above, a user having a requisite degree of pharmaceutical training and/or supervision should perform clinical interventions and non-clinical interventions do not require a requisite degree of pharmaceutical training. Table I, below, lists examples of interventions. There may be other interventions and the Table I should not be construed as limiting.

TABLE I

Intervention Examples

| Type | Complete Warning Message | Edit Sheet Text/Notes | Response |
| --- | --- | --- | --- |
| AL | The patient is allergic to Ceftriaxone Sodium. Your action is (N)ot fill or (O)verride and continue filling | Allergic to Ceftriaxone Sodium. | |
| ALCS | The patient may exhibit a cross-sensitive allergic reaction to Ceftriaxone Sodium. Your action is (N)ot fill or (O)verride and continue filling | Patient may be cross-sensitive to X. (where xX = drug cross sensitivity to) | n, o, / |
| AO | This order has never been discontinued. Continue processing a duplicate new order or (D)iscontinue this order and generate new one? | Text if response "Y" (yes): "Duplicate new order entered". Text if response "D" (discontinue old RX): "Previous RX discontinued, new order created." | Y, D |

TABLE I-continued

Intervention Examples

| Type | Complete Warning Message | Edit Sheet Text/Notes | Response |
|---|---|---|---|
| AO | This item has already been entered but not yet verified. Do you want to continue entering this new order for the same item? (y/n) | Duplicate item already entered but not yet verified. Order # X (where x is the OEL ID) | Y, N, / |
| AO | This item has already been ordered. Enter (Y)es to continue processing a duplicate new order, (N)ot fill, or (R)efill R1088. | Item has already been ordered for this patient under RX # R1088. | Y, N, R, / |
| C2 | Class 2 narcotic. Do not refill until a hardcopy prescription has been received from the physician. Continue? <if "y"> partial filling permitted up to prescribed quantity and 60 day supply | Class 2 narcotic, Hardcopy received? | Y, N, / |
| CIS | <drug> is absolutely contraindicated for patients with <diagnosis>. Continue anyway? | <drug> is contraindicated for patients with <diagnosis>. | Y, N, / |
| CIS | <drug> should be used with caution for patients with <diagnosis> continue anyway? | <drug> should be used with caution for patients with <diagnosis>. | Y, N, / |
| CO | This order can only be charted, it cannot be filled | Text: Chart only order. | |
| COM | This order originated from company 1, continue anyway? | Text: Order originated from Company 1. | Tech must answer |
| DA | This patient's account is past due 15 days. Release of this order requires E.D. approval. Continue? | Account is past due 15 days. Display text user entered | Y, N, / |
| DA | This patient's account is past due 15 days. This patient's balance ($2198.57) exceeds their credit limit of $500.00. Release of this order requires E.D. approval. Continue? | Account is 15 days past due & over their credit limit of $500.00. Balance due $2198.57. Display text user entered. | Y, N, / Plus reason text |

Table I lists examples of both clinical-type and non-clinical-type interventions (here referred to as "Warnings"). The "Edit Sheet Text/Notes" column shows the intervention message as it would appear on screen and made available to a user. The edit sheet text is abbreviated and the complete warning is displayed in the "Complete Warning Message" column. The "Response" column indicates the required response by a user associated with a respective intervention message. In certain cases, the appropriate response requires a computer entry, such as entering a "Y" for yes or an "N" for no.

Referring again to FIG. 4 an example of a workflow model for routing tasks to users is shown. The lines connecting the elements indicate communication rather than physical connections between the elements. A pharmaceutical order is fully entered at order entry. As shown by dotted lines, data can be entered by a technician and/or pharmacist prior to order entry, as noted above. Based on a computerized (and/or user) analysis of the data associated with the order, the system associates a non-clinical intervention with the order. The system adds the non-clinical task to a billing user's workflow at billing 60 and adds verification-related tasks including, where applicable, clinical intervention-related tasks to the verifying pharmacist's workflow at order verification 18. In this embodiment, the verifying pharmacist and the billing user can work to satisfy their respective intervention in parallel and each may or may not be aware of the other's assigned interventions associated with a particular prescription order. For example, in some embodiments, the billing data may not be available to the verifying pharmacist for pharmacist review (e.g., because the billing intervention does not appear on the verifying pharmacist's order review screen; see FIG. 8). In some embodiments, tasks are added sequentially where one or more interventions must be satisfied before other interventions can be satisfied or even routed. In some cases, tasks may be routed simultaneously along differing workflows, but action on a particular task may be on hold until a different intervention is satisfied first.

Referring still to FIG. 4, the triage pharmacist can also receive tasks that are routed through the system from the verifying pharmacist at order verification 18. However, as noted above, because the triage pharmacist is involved in identifying and resolving clinical issues, the verifying pharmacist's primary tasks are typically those related to verifying that orders are entered into the system properly (e.g., through online verification and/or output/label match). In some embodiments, however, the verifying pharmacist may be involved in clinical review of orders, such as new order and refills with changes (clinical review may include drug interactions, therapeutic duplication, proper indication, no contradictions, correct dosage (frequency and dose) and allergies, as examples), which can allow for a check of any missed clinical or other issues, e.g., requiring an intervention. Examples of tasks that may be routed from the verifying pharmacist to the triage pharmacist include those involving non-resolved clinical issues and data input errors. Once the triage pharmacist works an intervention, e.g., by placing calls, doing research, etc., the order is routed for a visual check (e.g., by the verifying pharmacist) and then routed to a clinical and billing approval queue 62 until both the clinical and non-clinical interventions are worked. In some cases, as shown, it may be desirable to route the order back to order entry for data re-entry (e.g., where a clerical error has been made). After the interventions have been satisfied, the order is placed in the label allowed queue.

Figure 7:
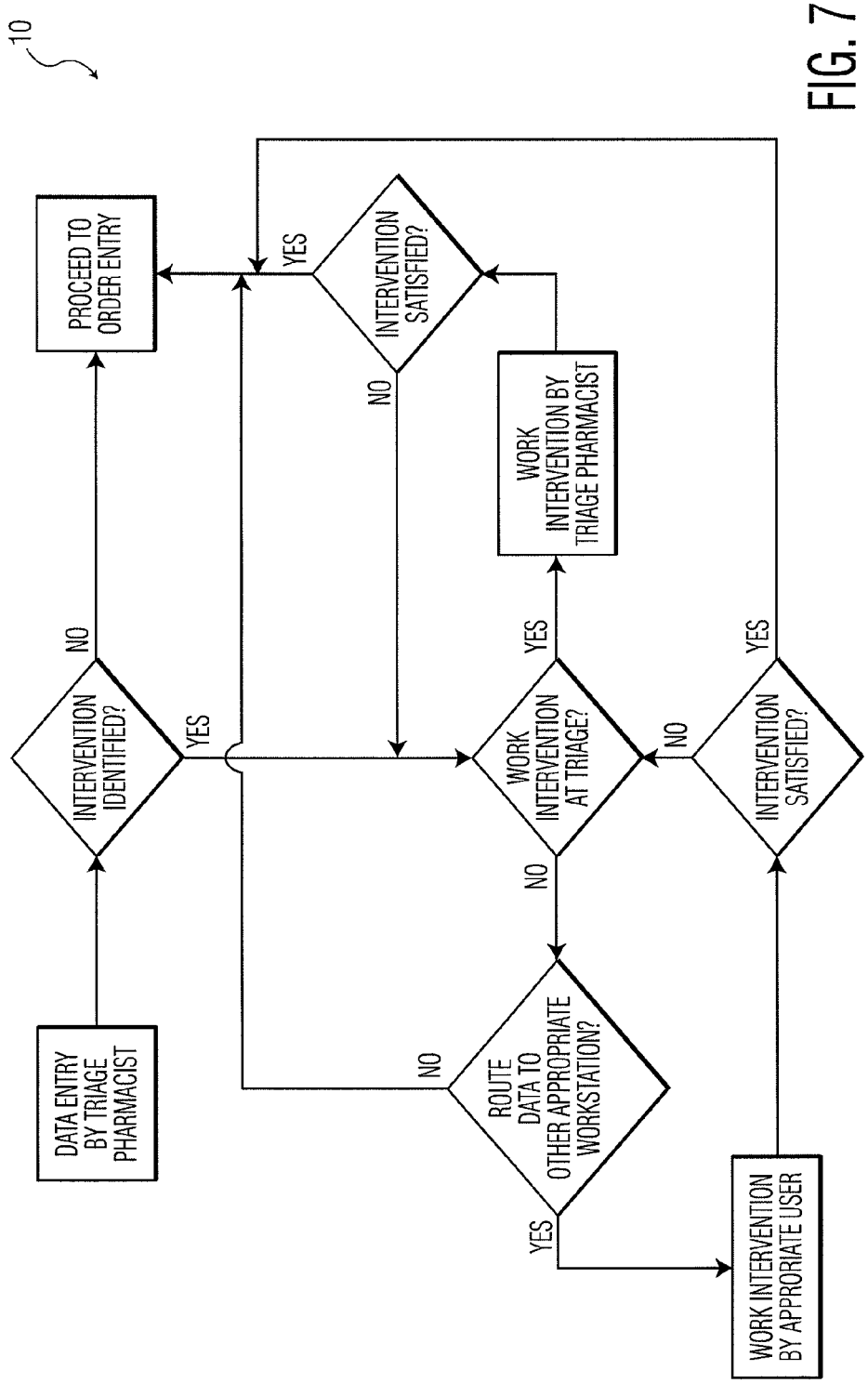
FIG. 7 is a pre-order entry workflow embodiment for use in the process of FIG. 1.

FIG. 7 is another workflow example 100 involving a triage pharmacist at triage 50. In this example, selected data such as patient name, prescribed drug, etc. is entered into the system. The system determines whether any interventions should be associated with the order based on the selected data entered (there may also be interventions assigned downstream of triage, such as at order entry 12 and/or order verification 18). If there are no interventions assigned to the order based on an analysis of the selected data, then the order can proceed to order entry. If an intervention is associated with the order, then it is determined whether the intervention should be worked by the triage pharmacist or routed to a different user, such as at billing 60 (FIG. 4). As described above, routing of data associated with the order can be based on the type of intervention and associated identifier.

In some cases where the intervention is satisfied by the triage pharmacist, the order may proceed to order entry. In some cases, there may be other interventions associated with the order that are routed to other users which can be (or may not be) satisfied before routing the order to order entry. If an intervention is routed to a user other than the triage pharmacist, that user may satisfy the intervention and then the order may be routed to order entry. In certain cases, the type of intervention may be such that the order can proceed directly to order entry without working the intervention at a pre-entry step. For example, an intervention may be associated with an order at triage 50 and the order can proceed to order entry and data including the intervention associated with the order can be accessed by the order verifying pharmacist. Prior to (or subsequent to) order entry, the intervention may be worked by the order verifying pharmacist at order verification 18. Other work flow examples are possible.

Packaging, Labeling and Delivering

When a label is printed, the label can taken by a user (e.g., a technician), who retrieves or "picks" the corresponding prescription and the label is attached to the prescription and placed into a delivery tote. The label may include a warning assigned by the system and/or a warning assigned by a pharmacist. In some cases, a warning may be assigned automatically by the system, e.g., utilizing a Label Warning Code System (LWC), available from First DataBank, Inc., San Bruno, Calif., that assigns a generic sequence number (and/or name) for one or more medications requiring the same label warning (FIG. 5 shows a screen shot of a generic sequence code list 90). Alternatively, the pharmacist may assign a label warning, e.g., by selecting an appropriate warning from a list 92 of warnings stored in the system (see FIG. 6 for examples of warnings).

Figure 8:
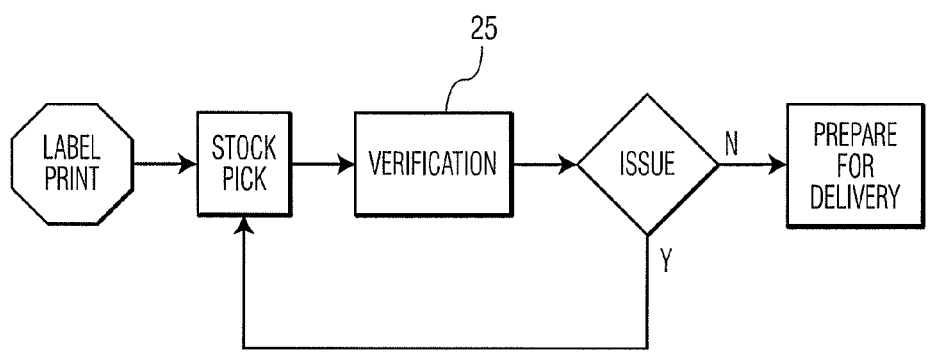
FIG. 8 is a flow diagram of a product verification embodiment for use in the process of FIG. 1.

Referring now to FIG. 8, the second pharmacist at the product verification step 25 can be used to verify that the product picked is the same item as printed on the label and also can act as an overall quality checking station (e.g., no broken pills, no missing bubbles, etc.). Other checks performed by the pharmacist at the second order verfication step 25 may include, for example, proper dose, proper packaging, proper labeling, proper warning stickers, proper route of drug administration and proper directions. As above, the pharmacist (or system) may re-route order data from the second order verification 25, e.g., to the triage technician, clinical pharmacist at the order verification step 18, pick technician and/or billing 60, if necessary.

In some embodiments, a dedicated pharmacist order-to-drug verification scan may be introduced where the system may prompt the product verification pharmacist for only a product scan of the package barcode 38 and a label scan of the label barcode 36, not requiring or even responding to a scan by the product verification pharmacist of the container barcode 30. In these embodiments, it may be desirable to introduce a dedicated order-to-tote verification scan performed by a technician following product verification 25 where the system may prompt the technician for only a scan of the container barcode 30 and a scan of the label barcode 36, not requiring or even responding to a scan by the technician of the package barcode 38.

In some embodiments, the verifying pharmacist is required to verify all products at the second verification step 25. Alternatively, it may be desirable, in some cases, to allow certain orders to bypass the second verification step and, e.g., require only a tote scan. Routing orders, e.g., based on whether they are new, refill, etc., is described in greater detail in pending U.S. patent application Ser. No. 10/610,681, filed Jul. 2, 2003, the entire content of which is hereby incorporated by reference as if fully set forth herein.

A user (e.g., technician and/or pharmacist) takes a labeled prescription and scans the delivery tote, the prescription label and the prescription, as noted above with reference to FIG. 1. In some cases, the system can be configured to require input by the user whenever an error is encountered and, e.g., the labeled product should not be placed in the tote. For example, the system may require a scanning technician entry, such as the term "GO" whenever an error is encountered. Examples of typical scanning errors include the order placed in the wrong tote, the fill has been cancelled and the order has not been verified by a pharmacist. A unique scanning sound may be used whenever a scanning error is encountered, which can aid the user in differentiating a scanning error from a successful scan. In some embodiments, one or more printers for printing labels are assigned to a pre-selected pick location. This arrangement can allow for labels of respective products to be printed nearby the pick location including the respective products, e.g., to minimize pharmacy traffic. Also, technicians may be assigned to specific picking locations.

Figure 9:
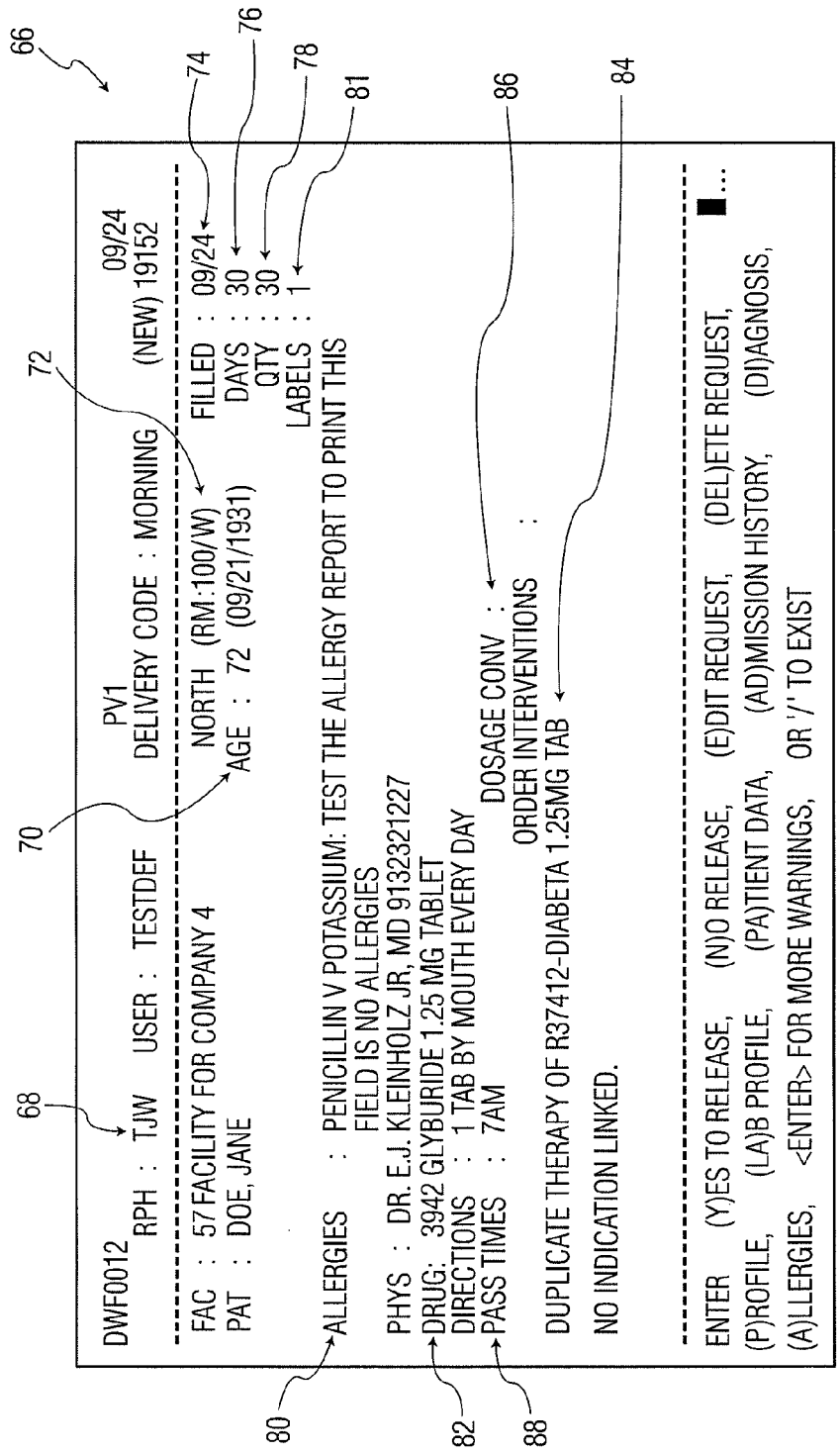
FIG. 9 illustrates an embodiment of an order review screen for use in the process of FIG. 1.

FIG. 9 shows an embodiment of a data review screen 66 containing routed data, such as may be used at order verification 18. The review screen 66 displays a pharmacist (RPh) code 68, patient age 70, patient date of birth (DOB) 72, patient allergies 80, fill date 74, days supply 76, fill quantity 78 and number of labels 81 to be printed. The drug name 82 and order interventions 84 are also shown and dosage conversion 86 is displayed adjacent to pass times 88. By entering the appropriate selection into the system, the verifying pharmacist can review the patient's admission history and patient drug diagnosis information. Pharmacists can also optionally update patient allergies. When an allergy is updated, drug allergy screening is reapplied to the patient's order currently under review to determine if any additional interventions are to be associated with the order. In some embodiments, the review screen may include triage pharmacist notes (not shown) that were entered prior to order entry 12. If an order is removed (e.g., by discontinue or by patient discharge), the review screen may further include a notice to this effect.

Status of an order (or batch of orders) can be tracked through the system. Referring to FIG. 10, an order status screen 70 allows a user, such as a technician or pharmacist, to receive information regarding the status and audit trail of an order. In some cases, the order status screen may include an audit record 72 for each time an order entry user, technician and/or pharmacist takes an action to satisfy an intervention, such as by canceling an order, as an example. It also provides information regarding where a specific prescription order may be paused in the pharmacy. Referring to FIG. 11, a daily order status screen 74 displays the number of orders queued at each station, which can aid in identifying bottlenecks in the process.

Any suitable architecture can be used to form a network for routing of data. In some cases, a peer-to-peer architecture may be used in which computing devices—desktop and laptop computers, hand held computers, servers, etc.—link directly to each other. This can include any suitable client-client and client-server connection using, for example, a local area network (LAN) or a wide area network (WAN) including the Internet. For example, workstations, e.g., used for order entry and/or order processing, may be connected to a server that can receive data from the workstations and distribute or provide access to data to certain ones or all of the workstations according to predetermined processing rules. Alternatively, some or all of the workstations may be able to process and distribute order data to certain other one or more workstations according to predetermined processing rules.

A number of detailed embodiments have been described. Nevertheless, it will be understood that various modifications may be made in the scope of the invention. For example, the system 10 can be configured to detect the discontinuation of medication to a patient. If discontinuation of medication is detected, the system can associate an appropriate intervention with the order. A user, such as the triage pharmacist, can respond to the intervention by determining why the medication was discontinued, assessing for potential impact to the patient and responding, if appropriate. For example, the user, in some cases with the system's assistance, can search for alternative medications to replace the discontinued medication. Accordingly, other such embodiments are within the scope of the following claims.

What is claimed is:

1. A method for electronically assisting in dispensing pharmaceuticals to patient care facilities, the method comprising:
    receiving a prescription order;
    conducting a triage data entry on the prescription order, the triage data entry comprising the steps of:
    determining if an intervention is associated with the prescription order, the intervention being clinical or non-clinical;
    if there is no associated intervention, proceeding to order entry;
    if there is an associated intervention, determining if the intervention is clinical or non-clinical, and if it is clinical, resolving the intervention with the assistance of a pharmacist and then proceeding to order entry;
    if the intervention is non-clinical, passing the prescription order to a further work station for resolution of the non-clinical intervention, and once resolved, then proceeding to order entry;
    conducting the order entry on the prescription order by entering data associated with the prescription order into a computer system including an intervention database;
    based on features of the order, associating with the order an intervention from the intervention database, the intervention being associated with a route through the system; and
    routing data associated with the prescription order along the route associated with the intervention;
    wherein the intervention includes an identifier that identifies a route through the system, further comprising:
    checking the prescription order, the step of checking comprising comparing the prescription order to the entered data;
    once the prescription order is checked, generating a prescription label to be placed on a prescription medication in accordance with the prescription order, the prescription label including a first barcode identifying the medication, the patient and the patient care facility;
    thereafter verifying the type and quantity of product identified in the prescription order, said step of verifying comprising:
    scanning the first barcode and a second barcode disposed on the prescription medication to determine that the prescription medication is in conformity with the prescription order; and
    if the first and second barcodes agree, placing the prescription medication in a delivery tote for delivery to the patient care facility; and if not, redirecting the prescription medication for further review;
    the delivery tote having a third barcode identifying the patient care facility, and if the first and second barcodes agree, scanning the third barcode to determine that the prescription order is correctly associated with the delivery tote.

2. The method of claim 1, wherein the identifier is in the form of a numeric code.

3. The method of claim 1, wherein the system comprises at least two networked computers.

4. The method of claim 3, wherein the step of routing data associated with the prescription order comprises routing data associated with the prescription order from a first computer to a second computer.

5. The method of claim 1, wherein the data associated with the prescription order is entered into the system using a computer.

6. The method of claim 1 further comprising verifying that the data entered is consistent with the associated prescription order.

7. The method of claim 6 further comprising generating an electronic edit list for use in the step of verifying.

8. The method of claim 1 further comprising tracking the order using barcode technology.

9. The method of claim 1 further comprising:
    based on the data, detecting discontinuation of medication to a patient; and associating an intervention with the order if discontinuation of medication is detected.

10. A computer implemented process for dispensing pharmaceuticals to patient care facilities, the process comprising:
    conducting a triage data entry on each prescription order of a batch of new prescription orders, comprising the steps of:
    determining if an intervention is associated with each prescription order, the intervention being clinical or non-clinical;
    if there is no associated intervention, proceeding to order entry;
    if there is an associated intervention, determining if the intervention is clinical or non-clinical, and if it is clinical, resolving the intervention with the assistance of a pharmacist and then proceeding to order entry;
    if the intervention is non-clinical passing the prescription order to a further work station for resolution of the non-clinical intervention, and once resolved, then proceeding to order entry;
    conducting the order entry on each prescription order by entering data relating to the batch of new prescription orders into fields of a computer system, the fields receiving data relating to a pre-selected set of features of respective new prescription orders;
    classifying the new prescription orders of the batch into a first class of new prescription orders and a second class of new prescription orders based on the data entered;
    routing data associated with the first class of new prescription orders along a first route through the computer system; and routing data associated with the second class of new prescription orders along a second route through the computer system, the second route being different than the first route, wherein the first class of new prescription orders consists of new prescription orders having an associated clinical intervention; and wherein the second class of new prescription orders comprises new prescription orders having an associated non-clinical intervention; and further wherein each intervention includes an identifier that identifies a route through the system; further comprising:

checking the prescription order, the step of checking comprising comparing the prescription order to the entered data;

once the prescription order is checked, generating a prescription label to be placed on a prescription medication in accordance with the prescription order, the prescription label including a first barcode identifying the medication, the patient and the patient care facility;

thereafter verifying the type and quantity of product identified in the prescription order, said step of verifying comprising:

scanning the first barcode and a second barcode disposed on the prescription medication to determine that the prescription medication is in conformity with the prescription order; and if the first and second barcodes agree, placing the prescription medication in a delivery tote for delivery to the patient care facility; and if not, redirecting the prescription medication for further review;

the delivery tote having a third barcode identifying the patient care facility, and if the first and second barcodes agree, scanning the third barcode to determine that the prescription order is correctly associated with the delivery tote.

11. The process of claim 10, wherein the step of entering data is performed by a pharmacist.

12. The process of claim 10 further comprising determining whether to associate with respective new prescription orders one or more interventions based on the data.

13. The method of claim 10 further comprising detecting discontinuation of medication to a patient.

14. The process of claim 10, wherein at least one of the first and second classes of new prescription orders consists of new prescription orders having no associated intervention.

15. The process of claim 10, wherein the step of entering data includes entering a note into the computer system, the note being associated with a respective new prescription order.

16. The process of claim 15, wherein the step of routing data associated with the first class of new prescription orders includes routing the note associated with the respective new prescription order.

* * * * *